US006703235B2

(12) United States Patent
Luebke et al.

(10) Patent No.: US 6,703,235 B2
(45) Date of Patent: Mar. 9, 2004

(54) COMPLEX MULTICELLULAR ASSEMBLIES EX VIVO

(75) Inventors: Kevin J. Luebke, Dallas, TX (US); Kathlynn C. Brown, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 15 days.

(21) Appl. No.: 09/888,895

(22) Filed: Jun. 25, 2001

(65) Prior Publication Data

US 2003/0013080 A1 Jan. 16, 2003

(51) Int. Cl.[7] ................................................. C12M 3/00
(52) U.S. Cl. ................................ 435/283.1; 435/286.2; 435/292.1; 435/305.1; 435/309.1; 435/402
(58) Field of Search ........................... 435/283.1, 286.2, 435/286.3, 292.1, 305.1, 309.1, 309.4, 1.1, 397, 398, 402

(56) References Cited

U.S. PATENT DOCUMENTS 4,996,154 A * 2/1991 Gabriels, Jr. ................ 435/350
5,412,087 A * 5/1995 McGall et al. ............... 536/24.3
5,482,867 A * 1/1996 Barrett et al. ................ 436/518
6,271,957 B1 * 8/2001 Quate et al. ................. 359/298
6,541,022 B1 * 4/2003 Murphy et al. .............. 424/422

FOREIGN PATENT DOCUMENTS

| EP | 531733 A1 | * 3/1993 | ............ C12N/5/00 |
| WO | WO 01/19504 | 3/2001 | |
| WO | WO 01/19505 | 3/2001 | |

OTHER PUBLICATIONS

Furuta et al. Brominated 7–hydroxycoumarin–4–ylmethyls: Photolabile protecting groups with biologically useful cross–sections for two photon photolysis. Proc. Nati. Acad. Sci. vol. 96 (Feb. 1999), pp. 1193–1200.*

* cited by examiner

Primary Examiner—William H. Beisner
(74) Attorney, Agent, or Firm—Gardere Wynne Sewell LLP

(57) ABSTRACT

Various embodiments of the present invention provide both apparatus and method for the patterning of cells onto non-adhesive substrates and the controlled regulation of cells through the use of photoactivated cellular morphogenic factors.

19 Claims, 3 Drawing Sheets

COMPLEX MULTICELLULAR ASSEMBLIES EX VIVO

FIELD OF THE INVENTION

The present invention relates generally to the field of forming multi-cellular assemblies and specifically to a method for the arrangement and subsequent growth of cellular patterns ex vivo.

BACKGROUND OF THE INVENTION

Growth of functional, living tissues in vitro allows the replacement of diseased or damaged tissue grown from the patient's own cells. For example, skin and cartilage have already been grown in vitro and used for tissue replacement. These are relatively simple tissues consisting of only a few cell types anchored on a meshwork of collagen. However, tissues often comprise many different types of cells arranged in complex three-dimensional patterns. A general method of tissue engineering requires the ability to control complex tissue morphogenesis.

Tissue morphogenesis is the process by which cells grow and differentiate into functional assemblies. Organization of different cell types into a defined architecture is directed by chemical signals that control each cell's growth, morphology, migration and differentiation. For a tissue to develop correctly, these signals must be presented at the right time and place. Creation of functional tissues in vitro requires the generation of a large number of morphogenic signals with high spatiotemporal resolution.

In order to achieve complex supercellular structures in vitro, biomolecules must be patterned with resolutions on the order of cellular dimensions. Defined patterns of cells on surfaces by patterning cell adhesion molecules to a surface and allowing cells to attach in the arrangement defined by the adhesion molecule have been demonstrated.

Biomolecular templates may be constructed by several conventional methods such as photolithography using micromachined masks, contact printing of self-assembled monolayers, or photochemical cross-linking of proteins or peptides. While these techniques are useful experimental tools, they suffer from limitations. First, the patterns generated with most of these methods are static structures that cannot be changed with time, and they are all limited to a single layer of cells. Furthermore, all but the photochemical cross-linking are limited to creating patterns of a single cell attachment protein.

Approaches that use pre-fabricated three dimensional scaffolds to direct the growth of cells have similar limitations in that they provide few chemical signals for the arrangement of cell types, with little spatial or temporal control over the presentation of chemical signals.

SUMMARY OF THE INVENTION

Various embodiments of the present invention provide both an apparatus and a method for the patterning of cells onto non-adhesive substrates and the controlled regulation of cells through the use of, e.g., photoactivated cellular morphogenic factors.

More specifically, one form of the present invention provides a method for the modification of a surface including the steps of obtaining a non-adhesive substrate and treating that substrate with a sensitizing agent and light so that the surface becomes sensitized to the attachment of biological moieties such as cells, viruses and/or fragments thereof.

Another form of the present invention is a method for immobilizing cells that includes the steps of contacting a portion of a substrate with a solution of a photoreactive sensitizing agent and exposing a portion of the substrate to a light source. Cells are then brought into contact with the surface and adhere based, e.g., on the location of light exposure of the sensitizing agent.

Yet another form of the present invention is a method for the sequential immobilization of cells including the steps of treating a portion of a non-adhesive substrate with a photoreactive sensitizing agent and exposing a portion of the substrate to a light source. One or more first cells are then contacted with the substrate, and any unimmobilized first cells are removed. The substrate is then treated again with the same or a different sensitizing agent and a different portion is exposed to the light source. One or more second cells are then contacted with the substrate.

Still another form of the present invention includes an apparatus for immobilizing cells including, a substrate that is non-adhesive to cells and a solution for treatment of the substrate. A light source irradiates a portion of the treated substrate, and a suspension of cells contacts the substrate.

Another form of the present invention is a method for the developmental control of cells including the steps of obtaining a substrate for cell attachment, contacting one or more cells with the substrate, and treating the attached cells with a light-activated cellular morphogenic factor. The light-activated cellular morphogenic factor is subsequently activated by exposing it to a light source.

An additional form of the present invention is an apparatus for the developmental control of cells. The apparatus includes a substrate for cell attachment and a light-activated cellular morphogenic factor. One or more cells that are contacted with the substrate and a light source that irradiates a portion of the substrate.

Another form of the present invention is a method for the developmental control of cells including the steps of obtaining a non-adhesive substrate and treating it with a sensitizing agent. The substrate is then exposed to a light source followed by contacting with a first biological moiety. The first biological moiety is then contacted with a light-activated cellular morphogenic factor and the cellular morphogenic factor is then activated by exposure to a second light source.

Another form of the present invention is a method for modifying the wetting properties of a substrate that is non-adhesive to cells. It includes the steps of obtaining a non-adhesive substrate and treating a portion of the substrate with a sensitizing agent and exposing a portion of the treated substrate to a light source.

1. Another form of the present invention is an apparatus that includes a non-adhesive substrate and a solution of treatment agent that contacts the non-adhesive substrate. a light source is also included that irradiates a portion of the treated non-adhesive substrate in preparation for contacting the surface with a suspension of cells.

BRIEF DESCRIPTION OF THE DRAWINGS

The above and further advantages of the invention may be better understood by referring to the following detailed description in conjunction with the accompanying drawings in which corresponding numerals in the different figures refer to the corresponding parts in which.

DETAILED DESCRIPTION OF THE INVENTION

Figure 1:
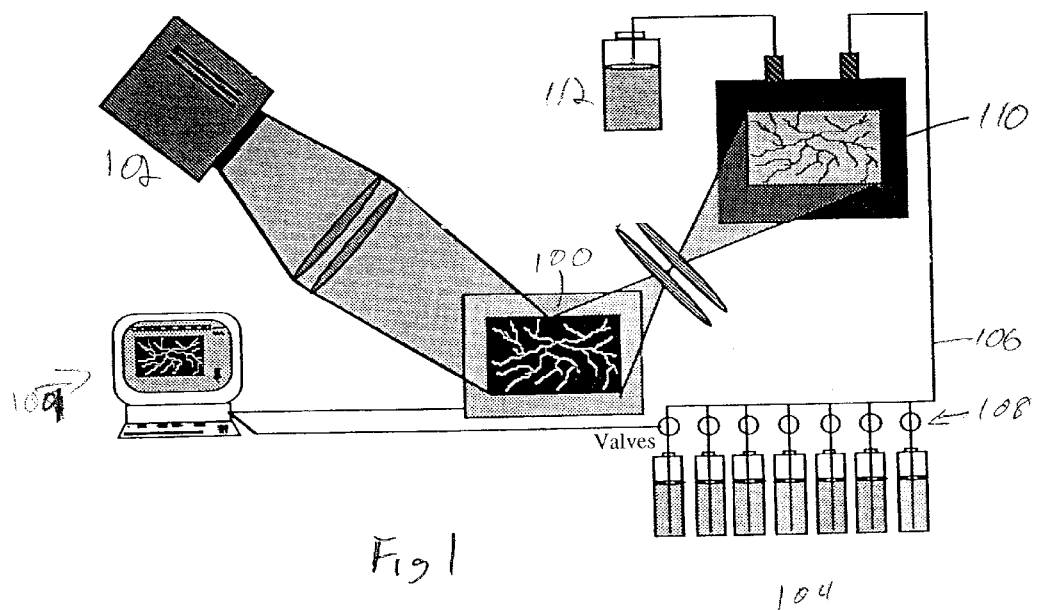
FIG. 1 depicts a light directed tissue growth device in accordance with the present invention.

While the making and using of various embodiments of the present invention are discussed herein in terms of cell patterning and selective control using light, it should be appreciated that the present invention provides many applicable inventive concepts that can be embodied in a wide variety of specific contexts. The specific embodiments discussed herein are merely illustrative of specific ways to make and use the invention and are not meant to limit the scope of the invention in any manner.

The following definitions are helpful in understanding the present invention:

Non-adhesive substrate or non-adhesive surface, it is meant herein that the surface compositions do not support attachment, spreading, or proliferation of normally adherent cell types.

Morphogen, or cellular morphogenic factor as used herein is defined as any chemical factor, naturally occurring or otherwise, the presence of which at some concentration or concentration gradient effects cellular development, including but not limited to cell shape, size, proliferation, growth, death, motility, state of differentiation, interaction with other cells, interaction with extracellular materials, or transcriptional, translational, or metabolic profile. A morphogen may exercise its effects on cells alone or in conjunction with other factors. Morphogens may include but are not limited to naturally occurring growth factors; proteins, peptides, peptoids, and small molecules identified by selection from chemical libraries; and molecules created by rational design and synthesis.

Light-activated or photoactivated cellular morphogenic factor as used herein is defined as any cellular morphogenic factor or morphogen for which some activity is altered, e.g., decreased or increased, by exposure to electromagnetic radiation of one or more wavelengths or combinations of wavelengths.

Light-directed cellular patterning and morphogenesis require a method of high-resolution illumination coupled with an automated system of fluid delivery. Such an apparatus is shown schematically in FIG. 1. One feature of this apparatus is its system of illumination, which relies on, e.g., a digital light processing technology from Texas Instruments. A digital light processor (DLP™) 100 is a micromachined array of mirrors, which is also referred to as a digital micromirror array.

Light is redirected or deflected by a micromirror array (Texas Instruments, U.S.A.). A computer controls the positioning of individual mirrors of the micromirror based on a pattern. The micromirror deflects the light into a lens that can focus or diffuse the light to illuminate a substrate. The lens can be magnifying or demagnifying, to set the size of the features on the substrate. The apparatus may also contain a shutter positioned between the light source and the micromirror in order to increase the acuity of light delivery to the micromirror. The shutter may also help increase the lifetime of the micromirror by decreasing the extent of direct and incident light that strikes the array of mirrors.

Current model digital light processors have, e.g., 480,000–2,000,000 mirrors, 17 um×17 um, in a 600×800 array, or greater. Each mirror is individually computer controlled to illuminate or not illuminate its corresponding image element by electrostatically flipping between two orientations. The mirrors flip within microseconds, so the pattern of illumination may be reconfigured nearly instantaneously.

The application of illumination technology to spatial control of photochemical reactions is particularly well suited to light-directed cellular morphogenesis for several reasons. For example, given the appropriate optics, the digital light processor can illuminate at single cell resolution; the size of each individually controlled image element may be the same as the size of each mirror, 17 um×17 um, which is approximately the same size as a mammalian cell. The projected image may be varied continuously under computer control, so a dynamic pattern of illumination can be used to direct cell growth, potentially with feedback from the tissue culture itself.

Conventional photolithographic patterning using physical masks may be used with the present invention, however they do not offer this advantage, because it requires, for example, a large number of masks, and considerable time is required to fabricate a mask with a given pattern. Time is also required to switch between physical masks, whereas the digital image can be changed in microseconds.

One feature of the digital light processor is that it also provides spatially resolved variation in incident light power by rapidly fluttering individual mirrors, a feature that is useful in creating density and concentration gradients. This feature is also inaccessible with conventional photolithographic methods, where illuminated areas all receive equivalent power or exposure.

Light-Directed Tissue Growth. An apparatus in accordance with the present invention is depicted in FIG. 1. The apparatus may be easily configured for a variety of applications. In addition to the digital light processor 100 and a lamp 102 as a light source, the device may be equipped with a fluidics system of pressurized bottles 104, tubing 106, and computer-controlled valves 108 for delivering reagents to the illuminated sample chamber and washing reagents from the chamber to a waste chamber 112. The lamp may be a mercury/xenon lamp, an argon laser, a diode pumped solid-state laser, a helium neon laser or any combination. It may also be any visible or ultraviolet light source, and may contain the 447 nm wavelength and/or the 365 nm wavelength.

The computer system 109 may be used to control the delivery of media, suspensions of cells, aqueous salt solutions and photoreactive morphogens. The computer system 109 may also control the digital light processor 100. The sample chamber 110 may contain, e.g., optically transparent windows separated by a thin fluid layer, or a matrix of gel or fiber mesh. One or both of the windows may be used as the substrate for cell growth. Materials occupying the volume between the windows may also be used as substrates for cell growth. The substrate for cell growth may include, at least in part, for example, a layer of polyethylene glycol or hydroxyethylmethacrylate. It may also include proteins or peptides.

Surface controlled cell patterning. The present invention may use the light-dependent alteration of surface properties or deposition of cell-adhesion molecules on a surface. Many cell-types will adhere to surfaces and many are anchorage-dependent, requiring attachment to a substrate in order to proliferate. Some cell types will adhere to a wide variety of substrate materials, while others require specific adhesion molecules. Specific surface-bound molecules will often affect the behavior of attached cells. For example, the arginine-glycine-aspartate (RGD) sequence from fibronectin supports adhesion and influences the behavior of numerous cell types.

Certain surface compositions, herein termed non-adhesive substrates, do not support attachment of most cell types. Examples are surfaces coated with various polyethylene glycols or hydroxyethyl methacrylate (HEMA). These non-adhesive substrates may be made substrates for cell attachment by chemical modification. Modification of the physical or chemical properties of the surface, such as wettability, or covalent attachment of certain specific cell adhesion peptides can result in an adhesive substrate for many cell types.

A number of approaches have been used to photochemically alter non-adhesive surfaces and render them substrates for cell attachment. For example, conjugation of a benzophenone moiety to a peptide containing the RGD motif affords a compound that can be photochemically attached to non-adhesive substrates and render those portions photochemically modified substrates for cell adherence. Such methods may be used in conjunction with the device and methods of the present invention.

One particular method makes use of a novel surface modification chemistry in which a metal complex such as tris(bipyridyl) ruthenium(II) chloride is activated by absorption of light and reacts in the presence of an electron acceptor with a variety of unsaturated organic compounds including tryptophan, tryptamine, a derivative or analogue of tryptophan or a peptide that includes tryptophan to modify the surface proximal to the site of illumination. This particular method has the advantages that it requires relatively low power illumination, it can be carried out using visible light rather than ultraviolet light, and does not require the conjugation of special non-native residues (such as benzophenone) to peptides.

Figure 2A:
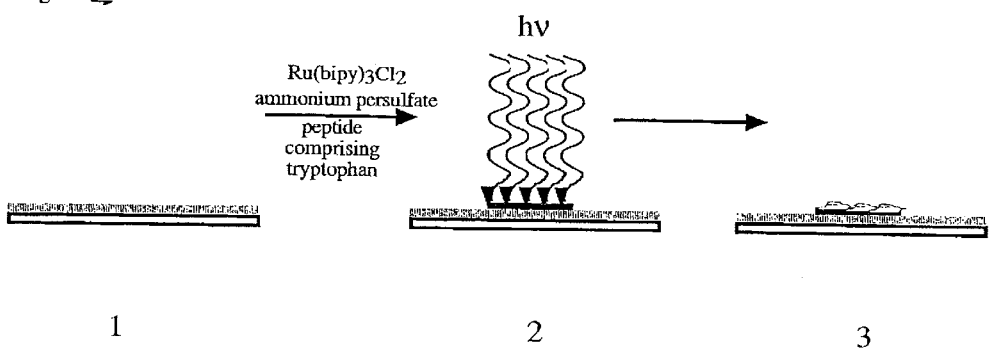
FIG. 2 depicts reactions and strategies in accordance with the present invention.

FIG. 2A(1) depicts one example of a non-adhesive surface. The surface may be rendered non-adhesive by coating with any of a variety of compositions including polyethylene glycol or hydroxyethyl methacrylate. Procedures for creating such surfaces are well known in the art. FIG. 2A(2) depicts a further example of selective alteration of non-adhesive surface. The surface is contacted with a solution containing a metal complex, such as tris(2,2'-bipyridyl) ruthenium(II) chloride, an electron acceptor such as ammonium persulfate, and a peptide that includes a tryptophan residue. While in contact with this solution, the surface of the substrate is irradiated with light at one or more wavelengths absorbed by the metal complex. Alteration of the surface renders it adhesive to cells, selectively, in the irradiated regions.

FIG. 2A(3) depicts a third example where cells are adhered preferentially to the area that had been altered selectively. Surface alterations that change the hydrophilicity, charge, or other physical properties of the surface lead to cell adhesion as can derivatization with selective cell-adhesion compounds, including but not limited to peptides such as Tyr-Ille-Gly-Ser-Arg (YIGSR) or Ill-Lys-Val-Ala-Val (KVAV) sequences from laminin or the Arg-Gly-Asp (RGD) sequence from fibronectin.

The present invention allows alteration of a non-adhesive surface in a pattern and exposure with that pattern in the attachment and subsequent growth of adherent cells on the surface. The resolution of the cellular pattern is assessed by light microscopy or fluorescence microscopy of stained cells or cells expressing a fluorescent protein. Because Digital Light Processing is particularly well suited to illuminating in intensity gradients, patterns of exposure may be created that lead to the creation of gradient cell densities on the substrate surface or in a matrix.

In operation, the present invention may be used in one example to produce adhesion and growth of two cell types are patterned together on a substrate. A non-adhesive substrate is mounted in the apparatus of the invention and covered with a buffered solution of tris (2,2'-bipyridy 1)ruthenium (II) chloride, ammonium persulfate, and typtamine. The surface is then illuminated in the desired pattern of adhesion of one cell type. After illumination, the solution is washed away, and the surface is washed with medium and covered with a suspension of cells, e.g., fibroblasts. After cells from this suspension have adhered to photochemically altered regions of the surface, non-adherent cells are washed away. Medium containing growth factors or serum is added and the cells are allowed to proliferate to the desired extent. The medium is then washed away with buffer and the substrate is again covered with a buffered solution of tris(2,2'-bipyridyl) ruthenium(II) chloride, ammonium persulfate, and tryptamine. Many cell types are unharmed by this treatment. A second pattern is illuminated. The solution is subsequently washed away and replaced with a suspension of a second cell type, e.g., keratinocytes. After cells from this suspension have adhered to photochemically altered regions of the surface, non-adherent cells are washed away. Medium containing growth factor or serum is added and two patterns of cells have been created.

Generation of cellular morphogenic factors in solution. An additional feature of the present invention is the ability to affect specific cellular responses by releasing active cellular morphogenic factors in a culture medium at specific locations on the substrate. With the described device, the region in space in which a morphogen is released can be precisely defined. Thus, cellular patterns can be created without relying on a chemically defined underlying substrate.

Figure 2B:
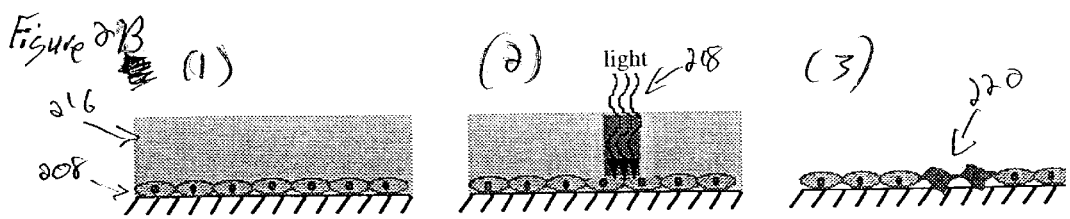

FIG. 2B depicts the selective differentiation of surface attached cells using a combination of light and exposure to a light activated cellular morphogenic factor. FIG. 2B(1) depicts surface attached cells 208 immersed in media 216 containing photomasked, i.e., photoprotected, cellular morphogenic factor. FIG. 2B(2) depicts using a light source 218 to activate, i.e., deprotect the cellular morphogenic factor in a specific location. FIG. 2B(3) depicts the result of the process showing that the cells 220 that were in the region where the light 218 was used to deprotect the photomasked cellular morphogenic factor have responded to the stimulus.

Several methods of creating light-activated chemical agents are known to those of skill in the art. A typical strategy involves masking critical chemical groups of the agent with a photolabile moiety, rendering the agent non-functional until the protecting group is removed by photolysis. Any photochemical protecting group is applicable to the present invention, and many are known to those with skill in the art. They include, but are not limited to, ortho-nitrobenzyl derivatives, such as (α-methyl-2-nitropiperonyl-oxy)carbonyl (MeNPOC), cinnamic acid derivatives, phenacyl derivatives, and hydroxycoumarin-4-yl-methanol derivatives. When the bioactive agent is a protein or peptide, a large number of surface-accessible side-chains can be protected by treatment of the protein or peptide with a chemically reactive derivative of the protecting group, such as a chloroformate or nitrophenylcarbonate. Alternatively, specific side chains can be protected by reaction with derivatives of the protecting group that react specifically with rare residues or by incorporation of photoprotected residues at specific positions during synthesis of the polymer.

In operation, the present invention may be used in one example as follows: a pattern of fibroblast cells is created by controlling the release of fibroblast growth factor (FGF). Growth of a non-confluent culture of fibroblast cells is arrested by placing the cells in serum-deprived medium, and cell proliferation is re-initiated by addition of FGF. A non-confluent layer of fibroblasts is maintained under serum-deprived conditions and placed in the apparatus of the present invention. A solution of the light-activated FGF is introduced, either manually or automatically by the apparatus. Light-activated FGF is generated by one of the schemes outlined above. FGF is deprotected in a spatially defined fashion, and patterned growth of the fibroblasts results.

The area of deprotection initially defines a steep gradient in active morphogen concentration. The activated morphogen will diffuse out of the area of deprotection. When undesirable concentrations of active morphogen arise due to diffusion outside of the region of deprotection, the medium is washed away rapidly and easily using the apparatus of the present invention, and a fresh solution of light-activated morphogen may be added. The rate of diffusion is modulated by adjusting parameters such as the viscosity or other transport properties of the medium. For example, the process can be carried out in a gelatin matrix, such as a collagen gel. The matrix would not only lower the rate of diffusion, but could also be used as a three-dimensional scaffold for cell growth.

In addition, several points should be noted with regard to diffusion of the light-activated morphogen. First, the effects of a morphogen are often not linearly related to morphogen concentration. Thus, diffusion of active morphogen into regions where its concentration is below a threshold of efficacy will not limit the resolution with which the morphogen's effects may be controlled. Second some desirable effects of morphogens are created by a gradient in morphogen concentration resulting from diffusion. Also, different effects can be created by the same morphogen at different concentrations. Thus diffusion of photoactivated morphogens can be used advantageously by allowing the concentration gradient that results to effect cell behavior. Third, in natural processes of tissue development and maintenance, multicellular structures are created by the diffusion of cellular morphogenic factors through the extracellular matrix and the gradients in morphogen concentration that result.

Three-dimensional control over cell life or death oon a three dimensional matrix of cells can be exercised over the light-dependent activation of cellular morphogenic factors by focusing a two-dimensional pattern of light in the desired plane. The light flux is highest and the photoactivation is most efficient in the plane of the focused image. Spatial resolution can be improved in this dimension by using light-activated morphogens for which absorption of two or more photons is required in order to produce active morphogen. This requirement can be created by masking the morphogen with more than one protective group or by using a single protective group with a large cross-section for two-photon release at a given wavelength.

A number of light-activated morphogens can be introduced into the system, either together or separately, thus adding layers of complexity to the cellular pattern. These features are unique to the system described.

In one example, glass slides were initially cleaned by placing them in a rack and soaking them in 30% wt/v sodium hydroxide for one hour with stirring. The slides were then well rinsed with deionized water (Milli-Q) and soaked in 1.2M hydrochloric acid for another hour. The sodium hydroxide wash was then repeated for a period of fifteen minutes and followed by rinsing with deionized water and drying overnight in a vacuum.

The surface of the glass slides was then silanized by immersion in 200 ml of glycidoxypropyltrimethoxy silane (Aldrich) and warming to 80° C. with stirring for six to eight hours. Warmed above 80° C. results in the slide having a cloudy appearance. After treatment, the slides were washed with acetone and acetonitrile and stored under vacuum overnight.

The silanized slides were coated with polyethylene glycol by immersion in PEG300 (Aldrich). Several drops of sulfuric acid were added, and the mixture was warmed to 80° C. with stirring for six to eight hours. After cooling the slides were washed with deionized water, dried in a stream of argon and stored under vacuum overnight.

Photochemical surface patterning was performed by treating the slides with a solution having the following properties: 0.2 to 2 mM tryptophan, tryptamine or tryptophan containing oligopeptide, 2 mM tris (2,2'-bipyridyl) ruthenium (II)chloride, 4 mM ammonium persulfate, 150 mM sodium chloride, and 15 mM phosphate. The solution had a pH of 7. Typically, 50 microliters of the solution were applied near the center of the slide and covered with a cover slip. The slide was supported horizontally with the solution on the upper surface and irradiated from below. Light was projected through a series of lenses from a digital micromirror array configured to reflect the desired pattern of cell adhesion. The micromirror array was illuminated with light from a 200 W Xe arc lamp that was passed through a bandpass filter, with maximum transmission at 447 nm (ca 60% transmittance) and a bandwidth at half-height of about 10 nm, for three to ten minutes. Following illumination, the slide was washed thoroughly with ethanol and then with deionized water. Patterned surface modification is usually apparent as differential wettability of the slide surface. The slide was stored in ethanol prior to cell-seeding.

Fibroblasts (NIH 3T3) were seeded on the patterned surface of the glass slide. The slide was placed in a 10 cm plastic culture dish and washed several times with RPMI medium. The medium contained no serum and no growth factors. The slide was then covered with 19 ml of RPMI medium. A nearly confluent layer of fibroblasts was then removed from its substrate with trypsin/EDTA and pelleted by centrifugation. The cells were then washed three times by suspending them in 7 ml of RPMI and re-centrifuged. Finally, they were suspended in 5 ml of RPMI. A 1 ml aliquot of the cell suspension was put into the dish containing the slide and the dish was incubated for four to six hours at 37° C. under an atmosphere of 5% carbon dioxide.

The culture was visualized by phase contrast microscopy and patterns of cell adherence were visible with the cells only adhering and spreading in the previously illuminated areas.

Photoreversible Inactivation of Basic Fibroblast Growth Factor and Reactivation with Light Inactivation. 6-Bromo-7-hydroxycoumarin-4-yl methyl p-nitrophenyl carbonate I was prepared by analogy to the method described by Furuta in *Proc. Natl. Acad. Sci. USA* 1999, 96, 1193–1200.

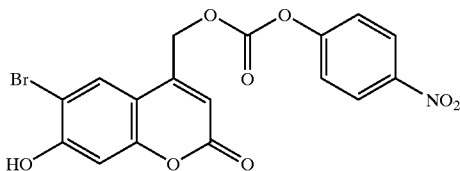

A solution of human recombinant basic fibroblast growth factor (25 ng/ml) and bovine serum albumin (1.25 mg/ml) in 100 mM sodium carbonate buffer, pH 10.5 was prepared. 40 microliters of the solution were mixed with 360 microliters of a solution of 1 mg/ml of 6-Bromo-7-hydroxycoumarin-4-yl methyl p-nitrophenyl carbonate in 100 mM sodium carbonate buffer at pH 10.5. The reaction was allowed to proceed for two hours at room temperature in the dark. The reaction was stopped by centrifugal gel filtration chromatography (spin column) through a column equilibrated with serum-free medium.

Reactivation. Aliquots of the growth factor, each containing 168 pg of the inactivated growth factor (described above), were irradiated for varying amounts of time in a quartz cuvette with 365 nm light. After irradiation, they were added to cultures of fibroblasts in serum-free medium. Cell proliferation was measured, and is graphed in FIG. 3.

Figure 3:
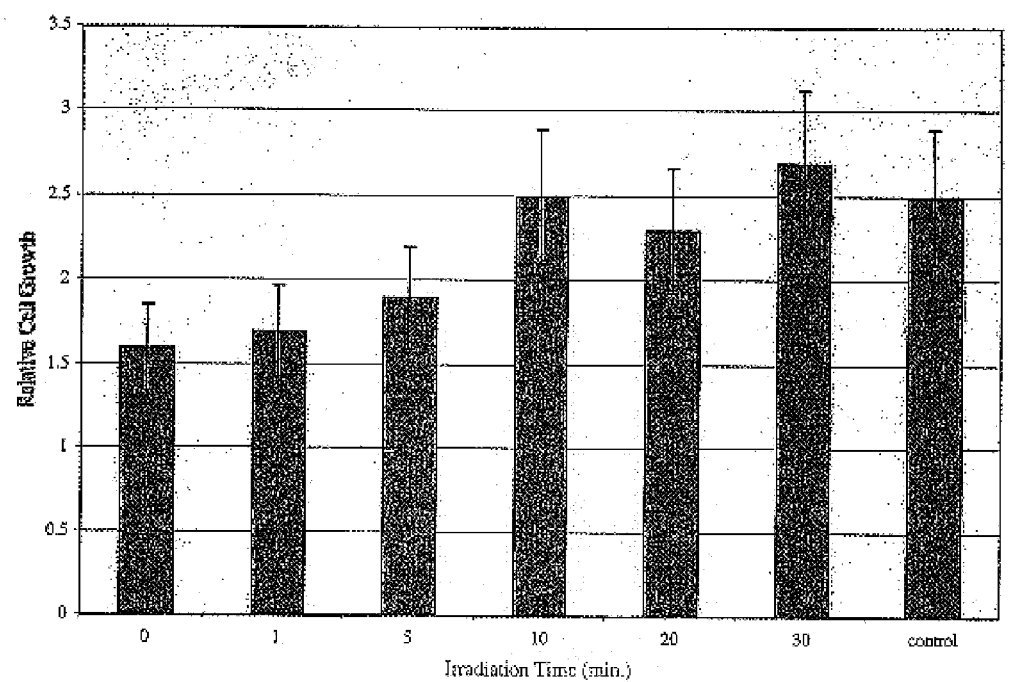
FIG. 3 depicts a graph of data measuring cell growth as a result of reactivating a photomasked cellular morphogenic factor in accordance with the present invention.

The data depicted in FIG. 3 show relative cell proliferation as a function of irradiation times. The cells in each culture were counted visually immediately after addition of the growth factor, and again 24 hours later. The ratio of the number of cells per unit area after 24 hours to the number of cells per unit area initially is plotted as Relative Cell Growth in FIG. 3.

While this invention has been described in reference to illustrative embodiments, this description is not intended to be construed in a limiting sense. For example, the term "computer" as used herein is to include any control apparatus capable of actuating a micromirror or micromirror array. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An apparatus for developmental control of cells comprising:
   a substrate for cell attachment;
   a light-activated cellular morphogenic factor patterned on the substrate; and
   a light source that irradiates a portion of the substrate for cell attachment.

2. The apparatus recited in claim 1, wherein the substrate for cell attachment comprises a polypeptide or protein.

3. The apparatus recited in claim 1, wherein the substrate for cell attachment comprises collagen.

4. The apparatus recited in claim 1, wherein the substrate for cell attachment is a matrix of gelatin or fiber.

5. The apparatus recited in claim 1, wherein the light-activated cellular morphogenic factor further comprises a masking group.

6. The apparatus recited in claim 5, wherein the light-activated cellular morphogenic factor is masked with a nitrobenzyl derivative.

7. The apparatus recited in claim 5, wherein the light-activated cellular morphogenic factor is masked with a halogenated hydroxycoumarin derivative.

8. The apparatus recited in claim 5, wherein the light-activated cellular morphogenic factor is masked with MeNPOC.

9. The apparatus recited in claim 5, wherein the light-activated cellular morphogenic factor is masked with a 6-Bromo-7-hydroxycoumarin-4-yl methyl derivative.

10. The apparatus recited in claim 1, wherein the light source comprises a visible light source.

11. The apparatus recited in claim 1, wherein the light source comprises a mercury/xenon lamp.

12. The apparatus recited in claim 1, wherein the light source is a diode-pumped solid-state laser, or a helium-neon laser, or a combination thereof.

13. The apparatus recited in claim 1, wherein the light source is a broadband ultraviolet lamp, or a mercury lamp, or a xenon lamp, or a combination thereof.

14. The apparatus recited in claim 1, wherein the light source comprises about 365 nm light.

15. The apparatus recited in claim 1, wherein the light source further comprises a micromirror array.

16. The apparatus recited in claim 15, wherein the micromirror array determines a pattern of exposure.

17. The apparatus recited in claim 16, wherein the pattern of exposure is focused in a predetermined position in order to activate the cellular morphogenic factor at that position.

18. The apparatus recited in claim 1, wherein the light-activated cellular morphogenic factor is a light-activated growth factor.

19. The apparatus recited in claim 1, wherein the light-activated cellular morphogenic factor is a light-activated fibroblast growth factor.

* * * * *